US008627820B2

(12) United States Patent
Matthiessen et al.

(10) Patent No.: US 8,627,820 B2
(45) Date of Patent: Jan. 14, 2014

(54) DEVICE FOR SUPPLYING A PATIENT WITH BREATHING GAS AND PROCESS FOR REGULATING A RESPIRATOR

(75) Inventors: Hans Matthiessen, Bad Schwartau (DE); Dieter Weismann, Gross Groenau (DE); Marcus Eger, Luebeck (DE)

(73) Assignee: Draeger Medical GmbH, Luebeck (DE)

( * ) Notice: Subject to any disclaimer, the term of this patent is extended or adjusted under 35 U.S.C. 154(b) by 1990 days.

(21) Appl. No.: 11/754,541

(22) Filed: May 29, 2007

(65) Prior Publication Data

US 2008/0000478 A1 Jan. 3, 2008

(30) Foreign Application Priority Data

Jul. 1, 2006 (DE) .......................... 10 2006 030 520

(51) Int. Cl.
*F16K 31/02* (2006.01)
(52) U.S. Cl.
USPC ................................ 128/204.23; 128/204.21
(58) Field of Classification Search
USPC ............. 128/200.24, 204.18, 204.21, 204.22, 128/204.23; 600/533
See application file for complete search history.

(56) References Cited

U.S. PATENT DOCUMENTS

| 3,292,623 | A | * | 12/1966 | Warren .................... 128/204.24 |
| 3,651,460 | A | * | 3/1972 | Gebelein, Jr. .............. 340/146.2 |
| 3,961,624 | A | * | 6/1976 | Weigl ....................... 128/205.23 |
| 4,031,885 | A | * | 6/1977 | Davis et al. ................... 600/533 |
| 5,184,292 | A | * | 2/1993 | Schneider ....................... 700/42 |
| 5,261,397 | A | * | 11/1993 | Grunstein ................. 128/204.18 |
| 6,068,602 | A | * | 5/2000 | Tham et al. ................... 600/533 |
| 6,626,175 | B2 | * | 9/2003 | Jafari et al. .............. 128/204.21 |
| 2002/0021241 | A1 | * | 2/2002 | Zhodzishky et al. .... 342/357.02 |
| 2003/0196663 | A1 | * | 10/2003 | Wenkebach et al. ..... 128/204.22 |
| 2004/0097821 | A1 | * | 5/2004 | Blomberg et al. ............ 600/529 |
| 2005/0005936 | A1 | * | 1/2005 | Wondka .................... 128/204.18 |
| 2005/0075531 | A1 | * | 4/2005 | Loeb et al. ...................... 600/17 |

* cited by examiner

*Primary Examiner* — Kristen Matter
(74) *Attorney, Agent, or Firm* — McGlew and Tuttle, P.C.

(57) ABSTRACT

A device for supplying a patient with breathing gas, in which an initially high initial pressure $P_{aw(t=0)}$ applied from the outside is automatically lowered by means of a control circuit to a lower inspiratory pressure $P_{aw(t)}$ as soon as a pulmonary internal pressure $P_{lung(t)}$ threatens to exceed a predetermined pulmonary target pressure $P_{lung,soll}$. Overinflation of the lungs due to the respiration is thus ruled out according to the present invention. The device permits, moreover, rapid filling of the lungs with breathing gas and makes thus possible a comparatively long phase of expiration. A process is also provided for regulating a respirator and for respirating a patient.

28 Claims, 3 Drawing Sheets

DEVICE FOR SUPPLYING A PATIENT WITH BREATHING GAS AND PROCESS FOR REGULATING A RESPIRATOR

CROSS REFERENCE TO RELATED APPLICATIONS

This application claims the benefit of priority under 35 U.S.C. §119 of German Patent Application DE 10 2006 030 520.5 filed Jul. 1, 2006, the entire contents of which are incorporated herein by reference.

FIELD OF THE INVENTION

The present invention pertains to a device for supplying a patient with breathing gas for setting a desired pulmonary target pressure ($p_{lung,soll}$), the device having at least one breathing gas delivery device for delivering breathing gas with an inspiratory pressure ($p_{aw(t)}$), and at least one means for determining a pulmonary internal pressure ($p_{lung(t)}$) during a respiration cycle, as well as a device regulating process and patient respiration process.

BACKGROUND OF THE INVENTION

Patients with chronic airway obstruction (so-called COPD—chronic obstructive pulmonary disease) have a persistent overload of their respiratory muscles, especially at the advanced stage of their disease. Due to the obstruction of the airways and the resulting increase in the airway resistance, they have to make a breathing effort that is several times that of healthy subjects. To guarantee sufficient ventilation, COPD patients at the advanced stage are therefore respirated in a pressure-controlled manner (PCV) when respiratory failure develops, in order to guarantee effective and sufficiently rapid filling of the lungs with breathing gas. At the same time, a comparatively long phase of expiration is desirable when respirating a COPD patient, because the patient must expire the volume of breathing gas breathed in essentially without mechanical support after opening an expiration valve. The comparatively long phase of expiration enables the patient to breathe out with the lowest possible effort. A sufficiently long expiration time is, moreover, necessary in COPD patients to avoid dynamic overinflation of the lungs as a consequence of "air trapping" with the development of an intrinsic PEEP (positive end-expiratory pressure) and increasing inspiratory breathing effort.

The physician has to pay attention to two general conditions now. On the one hand, a maximum pulmonary internal pressure reached $p_{lung,max}$ must not be exceeded, because lasting damage to the lung tissue could otherwise develop due to the pressure applied. On the other hand, a desired pulmonary target pressure $p_{lung,soll}$ inside the lungs should be reached as fast as possible after the beginning of the phase of inspiration of each respiration cycle. If the desired pulmonary target pressure $p_{lung,soll}$ is reached rapidly, early development of a sufficiently long end-inspiratory pressure plateau is possible in the range of the pulmonary target pressure $p_{lung,soll}$, and the diffusion processes between the blood and the breathing gas of the alveoli, which underlie the breathing, take place during this pressure plateau. It is also desirable to reach the pulmonary target pressure $p_{lung,soll}$ rapidly because the sooner the pulmonary pressure $p_{lung,soll}$ (and hence the end-inspiratory plateau pressure) is reached, the sooner can the phase of inspiration be concluded, and, due to this, the sooner the diffusion processes can be or are also concluded. Concluding the phase of inspiration as soon as possible—measured by the overall duration of each breathing cycle—in turn makes possible a comparatively long phase of expiration.

To meet both of the above-mentioned general conditions—avoidance of harmful pulmonary internal pressures and the shortest possible phase of inspiration or the longest possible phase of expiration—during the respiration of COPD patients, the respiration of such patients has so far been started at the beginning of each breathing cycle with a relatively high initial inspiratory pressure $p_{aw(t=0)}$ (initial pressure) markedly higher than the pulmonary target pressure $p_{lung,soll}$. With the intent to prevent damage to the lungs due to a rise in the pulmonary internal pressure $p_{lung(t)}$ at excessively high pressure values, the inspiration flow is interrupted after the end of a period set on the respirator and the inspiratory pressure $p_{aw(t)}$ is thus lowered to the desired pulmonary target pressure $p_{lung,soll}$.

However, this method is based on empirical values of the particular physician as well as on data from the literature and implies drawbacks and also health risks.

One risk lies in the fact that the physician selects the point in time at which he interrupts the inspiration flow to avoid a further increase in the pulmonary internal pressure above $p_{lung,soll}$ too late. Thus, there is a risk of damage to the lungs in case of and based on the respiration of the patient.

Another drawback of this procedure is that the physician lowers the initial pressure $p_{aw(t=0)}$ too early when he would like the avoid the above-described, excessively late stopping of the flow and thus the lowering of the respiratory pressure from the initial pressure $p_{aw(t=0)}$ to the correspondingly lowered inspiratory pressure $p_{aw(t)}$ with certainty. A comparatively late plateau may be formed as a result, the duration of the plateau may be too short, and the plateau pressure may be too low for the necessary diffusion processes. Furthermore, the beginning of the phase of expiration may be delayed, and the duration of the phase of expiration will be disadvantageously short.

Another drawback of this type of setting or predetermination of the respiratory pressures is that the general conditions of respiration may vary or change not only interindividually but also intraindividually. Thus, the physician's empirical values on the point in time at which the above-described pressure lowering shall take place do not apply equally to all patients. Moreover, the respiratory conditions applicable to a particular patient may change significantly in the course of the patient's disease and even during the respiration. The latter happens, for example, when the patient changes his position, attempts to actively support the respiration by his own respiratory activity, to counteract it and the like.

SUMMARY OF THE INVENTION

The object of the present invention is therefore to provide, while avoiding the drawbacks described above, a device for respirating a patient, which guarantees sufficient ventilation of the lungs or lung lobes (lungs for short) and at the same time allows sufficient time for the patient for expiration, while excessively high pressures in the lungs are to be prevented from developing. Another object of the present invention is to propose a process for regulating such a device according to the present invention as well as a process for respirating patients.

The device according to the present invention for supplying a patient with breathing gas is suitable for generating a desirable pulmonary target pressure $p_{lung,soll}$. The device has for this purpose at least one breathing gas delivery means for delivering breathing gas at an inspiratory pressure $p_{aw(t)}$, the breathing gas delivery means being a fan or another means suitable for this purpose.

The device according to the present invention has, furthermore, at least one means for determining a pulmonary internal pressure $p_{lung(t)}$ during a breathing cycle. By means of which process the pulmonary internal pressure $p_{lung(t)}$ is determined or measured is irrelevant according to the present invention. Even though preferred processes will be explained below, any process recognized by the person skilled in the art as being suitable for this purpose shall be covered by the present invention.

The pulmonary internal pressure $p_{lung(t)}$ prevailing at a point in time t is determined by means of the device during the phase of inspiration. It may be determined once within a breathing cycle; depending on the problem to be solved and/or the desired precision of the value for the pulmonary internal pressure $p_{lung(t)}$, it may, however, also be determined correspondingly frequently or even continuously during the phase of inspiration or during the entire breathing cycle.

At least the pulmonary target pressure $p_{lung,soll}$ desired during the phase of inspiration is able to be predetermined according to the present invention with the device according to the present invention, or the inspiratory pressure $p_{aw(t)}$ can be predetermined or set on the device to an initial pressure $p_{aw(t=0)}$ at a value above the pulmonary target pressure $p_{lung,soll}$. Provisions are therefore also made according to the present invention for setting, for example, only the pulmonary target pressure $p_{lung,soll}$ on the device and for the device itself always determining the initial pressure $p_{aw(t=0)}$ for example, at twice the value of the pulmonary target pressure $p_{lung,soll}$ so that it is sufficient for the physician to set only one pressure value before the respiration. Depending on the design of the device according to the present invention, it is, however, possible to predetermine both the pulmonary target pressure $p_{lung,soll}$ and the initial pressure $p_{aw(t=0)}$ independently from one another with the device.

The device according to the present invention is characterized in that it has at least one control means for regulating the inspiratory pressure $p_{aw(t)}$ on the basis of the pulmonary internal pressure $p_{lung(t)}$ and the pulmonary target pressure $p_{lung,soll}$.

It is thus possible according to the present invention to perform a pressure-controlled respiration of, for example, COPD patients, beginning with a comparatively high initial pressure $p_{aw(t=0)}$ (which may be, e.g., in the range of 65 hPa, while the initial pressure as well as the inspiratory pressure can be measured, in general, at the outlet of the device or, for example, at the Y-piece of a respiration line), in order to achieve as a result a rapid filling of the lungs, but without having to accept the risks and drawbacks occurring in connection with the use of conventional respirators, which were described in the introduction. Thus, there is no risk of an unintentionally long respiration with the comparatively high initial pressure $p_{aw(t=0)}$ until the pulmonary internal pressure $p_{lung(t)}$ has an unintended value above the pulmonary target pressure $p_{lung,soll}$. Unlike in the state of the art, the respiration with the device according to the present invention is not based on empirical values on when the pulmonary target pressure $p_{lung,soll}$ becomes established, but on the instantaneous pulmonary internal pressure $p_{lung(t)}$, i.e., the pressure given at a given point in time t being considered. This instantaneous pulmonary internal pressure $p_{lung(t)}$ may be determined according to the present invention as often as desired, so that the respiratory pressure (inspiratory pressure $p_{aw(t)}$) can be lowered in time from the initial pressure $p_{aw(t=0)}$ to a reasonable inspiratory pressure $p_{aw(t)}$ corresponding to the particular point in time during the respiration.

Based on this regulation of the inspiratory pressure $p_{aw(t)}$ to the instantaneous pulmonary internal pressure $p_{lung(t)}$, the onset of the plateau pressure is, moreover, prevented from being needlessly delayed, as this was described in the introduction as a drawback of the state of the art. Since the pulmonary internal pressure $p_{lung(t)}$ is known at any desired point in time or can be known in case of correspondingly frequent measurement or determination, it is also unnecessary when the device according to the present invention is used to lower the inspiratory pressure $p_{aw(t)}$ for safety reasons too early. The lungs of the patient being respirated can rather be filled with breathing gas as fast as possible until the pulmonary internal pressure $p_{lung(t)}$ reached corresponds to the desired pulmonary target pressure $p_{lung,soll}$. The lungs are now protected from damage due to an excessively high pressure even in case of rapid filling with breathing gas because of the regulation to the pulmonary internal pressure $p_{lung(t)}$.

Based on this regulation, the inspiratory pressure $p_{aw(t)}$ is advantageous and quasi automatically adapted to the respiration conditions, which are influenced, for example, by the repositioning of the patient.

Advantageous variants of the present invention are the subject of the subclaims.

Thus, the control means lowers the inspiratory pressure $p_{aw(t)}$ from the initial pressure $p_{aw(t=0)}$ in a preferred embodiment as a function of the difference between the pulmonary target pressure $p_{lung,soll}$ and the determined pulmonary internal pressure $p_{lung(t)}$. In another preferred embodiment, the inspiratory pressure $p_{aw(t)}$ is lowered to the pulmonary target pressure $p_{lung,soll}$ or can be lowered to this pulmonary target pressure $p_{lung,soll}$ In yet another preferred embodiment of the device according to the present invention, provisions are made for a maximum inspiratory pressure $p_{aw,max}$ to be able to be predetermined with the device such that respiration with an inspiratory pressure, which is above the predetermined inspiratory pressure $p_{aw,max}$, is not possible. This ensures a pressure regulation for safety at the outlet of the respirator, which advantageously ensures that acute lung damage because of a pressure that is harmful for the lungs cannot take place even in case of a possible erroneous determination or the development of another error. On the other hand, the pressure regulation for safety nevertheless permits respiration with an inspiratory pressure $p_{aw(t)}$ that is high enough to guarantee a necessary inspiratory flow to reach the desired pulmonary target pressure $p_{lung,soll}$.

In another preferred embodiment according to the present invention, the device has measuring means necessary for measuring a change in flow d(dV/dt) and a resistance R, which are known to the person skilled in the art. In another preferred embodiment, the changes in flow d(dV/dt) as well as the resistance R can be determined with these means, which advantageously makes it possible to determine the pulmonary internal pressure $p_{lung(t)}$.

The pulmonary internal pressure is determined by means of the equation $p_{lung(t)} = p_{aw(t)} - R \times dV/dt$ in this embodiment. Since at least $p_{aw(t)}$ and dV/dt can be determined or measured without effort on the part of the person skilled in the art with the device according to the present invention itself, and since the resistance R can also be determined without a special effort, which will be discussed below, it is possible according to the present invention with this embodiment to measure or determine the particular pulmonary internal pressure $p_{lung(t)}$ in a simple manner.

If a jump-back is used in the inspiratory pressure $p_{aw(t)}$ as a step function, as is proposed in another preferred embodiment according to the present invention, the resistance R can be determined from the formula R=dp/d(dV/dt). This determination of the resistance R enables the person skilled in the art to determine the resistance R without the noise and the invasiveness of a shutter and without loss of time during the respiration. The jump-back may be the pressure change dp between the initial pressure $p_{aw(t=0)}$ and the pressure to which the initial pressure $p_{aw(t=0)}$ is lowered. Both pressures can be measured with the device in a simple manner. The change in flow d(dV/dt) occurring now can also be easily determined.

The value determined for the resistance R is subjected to a plausibility check in yet another preferred embodiment according to the present invention. If the flow dV/dt that can be measured with the device according to the present invention does not equal zero when the pulmonary internal pressure $p_{lung(t)}$ and the pulmonary target pressure $p_{lung,soll}$ are equal after the plateau phase has been reached, it can be assumed that the resistance R determined by the device was determined with an error. It is therefore discarded and is not used, for safety reasons, in the calculation of the pulmonary pressure or other parameters. However, this result can be used to improve the measurement/estimation of the resistance. The measurement can be repeated. This procedure leads to additional operational reliability.

In yet another preferred embodiment, the regulation/determination of the pulmonary internal pressure $p_{lung(t)}$ can be achieved by means of one or more shutters, in which a flow dV/dt equaling zero is obtained. The advantages associated herewith are known to the person skilled in the art. Provisions are made for a corresponding plausibility check in yet another preferred embodiment by performing a comparison of the inspiratory pressure $p_{aw(t)}$ that becomes established after the plateau phase has been reached with the pulmonary target pressure $p_{lung,soll}$ at the flow dV/dt equaling zero, which is forced by means of the shutter. If these two values are not equal, the value calculated first for the resistance R is discarded and a new measurement is possibly carried out, with the advantage of increased process safety. This result can likewise be used to improve the measurement/estimation of the resistance.

The object according to the present invention is also accomplished by a process for regulating a device as well as by a process for respirating a patient.

All the advantages discussed above in connection with the device according to the present invention can also be achieved in full measure with the above-mentioned process regulating a device as well as by a process for respirating a patient. To avoid repetitions, reference is therefore expressly made to the above description and the description of the advantages achieved in this process.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
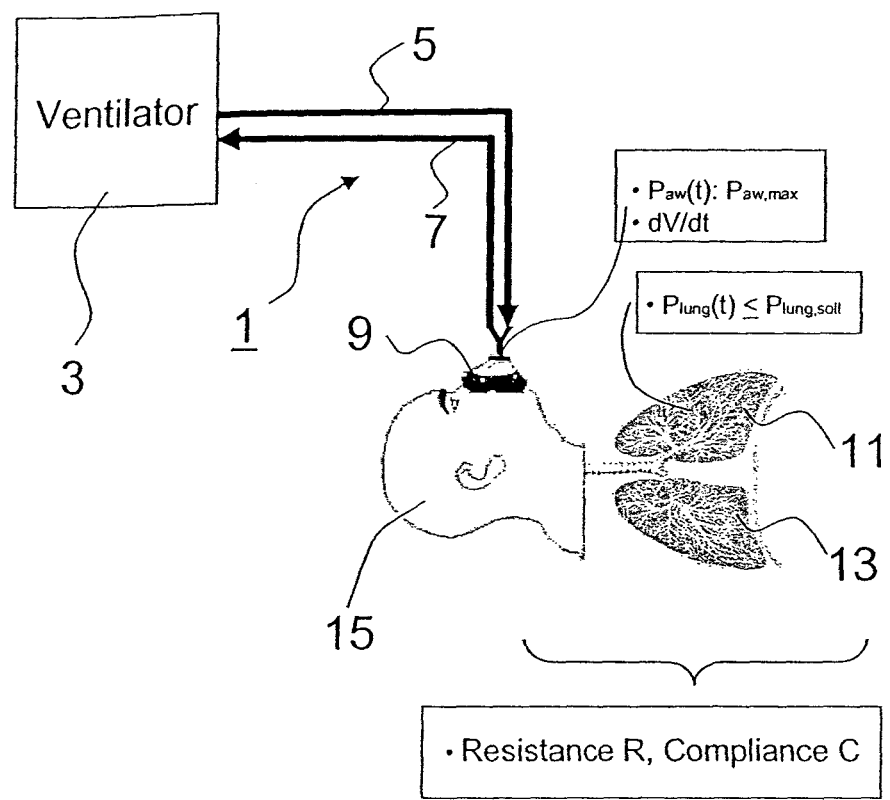
FIG. 1 is an overview of the system parameters used in connection with the present invention.

Referring to the drawings in particular, FIG. 1 shows essentially parameters that are used to explain the present invention and is intended to illustrate the assignment of these parameters to a patient 15 and/or to a device 1 according to the present invention.

The device 1 has a breathing gas delivery means in the form of a fan 3, by means of which a flow dV/dt can be moved into the lungs 11 and 13 of a patient 15 via breathing lines 5 and 7 and a face mask 9. The flow dV/dt is moved here with an inspiratory pressure $p_{aw(t)}$, which is always equal to or lower than a maximum inspiratory pressure $p_{aw,max}$ predetermined in preferred embodiments, against the airway resistance generated by the lungs or lung lobes 11 and 13. The pulmonary internal pressure $p_{lung(t)}$ becoming established in the lungs shall not exceed the pulmonary target pressure $p_{lung,soll}$.

Figure 2:
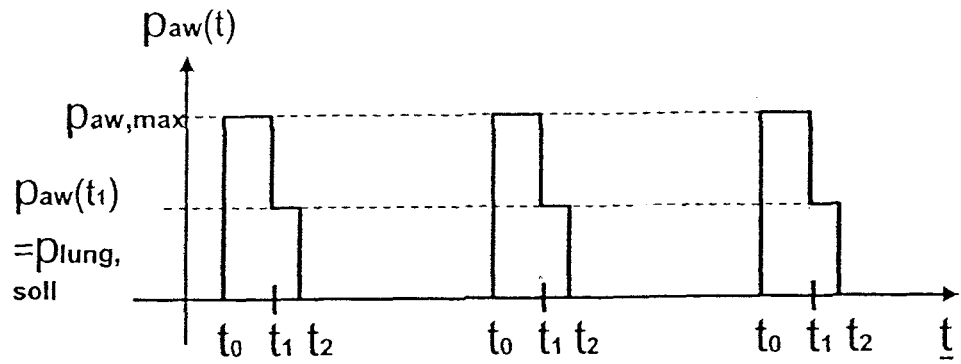
FIG. 2 is a view of curves as they can be obtained with the use of the device according to the present invention or the process according to the present invention.
Figure 2:
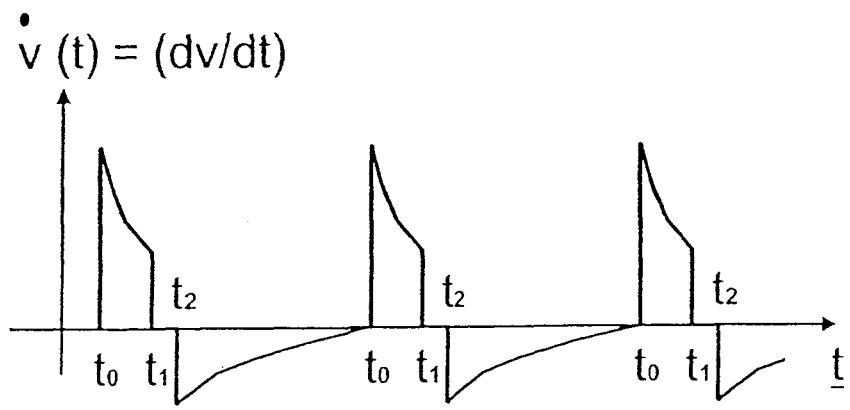
Figure 2:
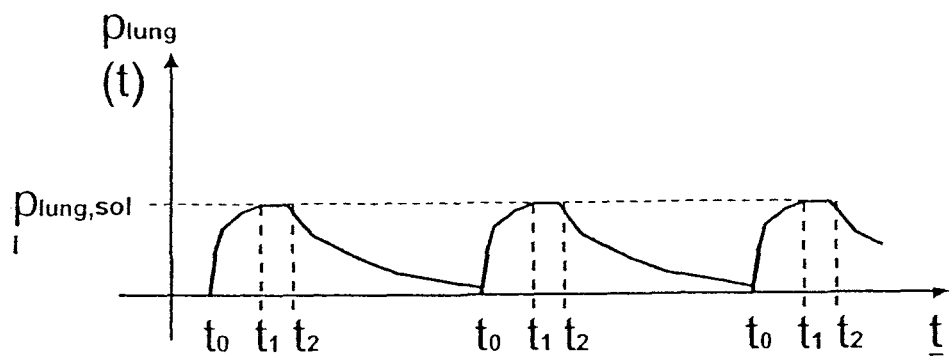

FIG. 2 shows possible curves of the inspiratory pressure $p_{aw(t)}$, the change in flow d(dV/dt) as well as the pulmonary internal pressure $p_{lung(t)}$ during the respiration of a patient 15 by means of the device 1 according to the present invention or the process according to the present invention.

A breathing cycle takes place as follows in the example of a respiration shown in FIG. 2: The inspiratory pressure $p_{aw(t)}$ shown in the upper view increases with the start of inspiration at time to or t=0 to an upper or maximum inspiration value $p_{aw,max}$ which corresponds to the initial pressure $p_{aw(t=0)}$ in this example, drives the flow dV/dt during the inspiration against the airway resistance or the resistance R into the lungs 11 and 13 and builds up the pulmonary internal pressure $p_{lung(t)}$ there (see lowermost view in FIG. 2) until the desired pulmonary target pressure $p_{lung,soll}$ becomes established. This pulmonary target pressure $p_{lung,soll}$ is reached in the lowermost view in FIG. 2 approximately at the time $t_1$. The initial pressure $p_{aw(t=0)}$ is regulated back to the inspiratory pressure $p_{aw(t1)}$ by back-regulation, and it assumes the same value as the pulmonary target pressure $p_{lung,soll}$ in the embodiment being described here. This value is maintained between the times $t_1$ and $t_2$, and the interval between $t_1$ and $t_2$ corresponds to the plateau phase. The flow dV/dt, whose course over time t is shown in the middle view in FIG. 2, is equal to zero between the times $t_1$ and $t_2$. The phase of expiration, during which negative flow values prevail, is between any time $t_2$ and the next later time to.

The jump-back from the upper pressure value $p_{aw,max}$ to the pulmonary target value $p_{lung,soll}$ can be used, as was described above, to determine the resistance R, without the flow dV/dt=0 having to be forced with a shutter. Should the flow not equal zero during the plateau phase, this is an indication of non-compensated leakages or muscle activity of the patient and thus of an invalid value for the determined resistance R.

After the end of the plateau phase, the respiration flow is set to zero on the device 1 at the time $t_2$ with the beginning of the expiration and the expiration valve is opened. The patient has sufficient time for breathing out now, because the lung was filled in a relatively short time by means of the comparatively high external pressure $p_{aw,max}$ and there was a sufficiently long plateau phase for the diffusion processes inside the lungs to take place. Based on the dynamic limitation of the pulmonary internal pressure $p_{lung(t)}$ by regulation, no overpressure hazardous to health has developed in the lungs in this case.

Figure 3:
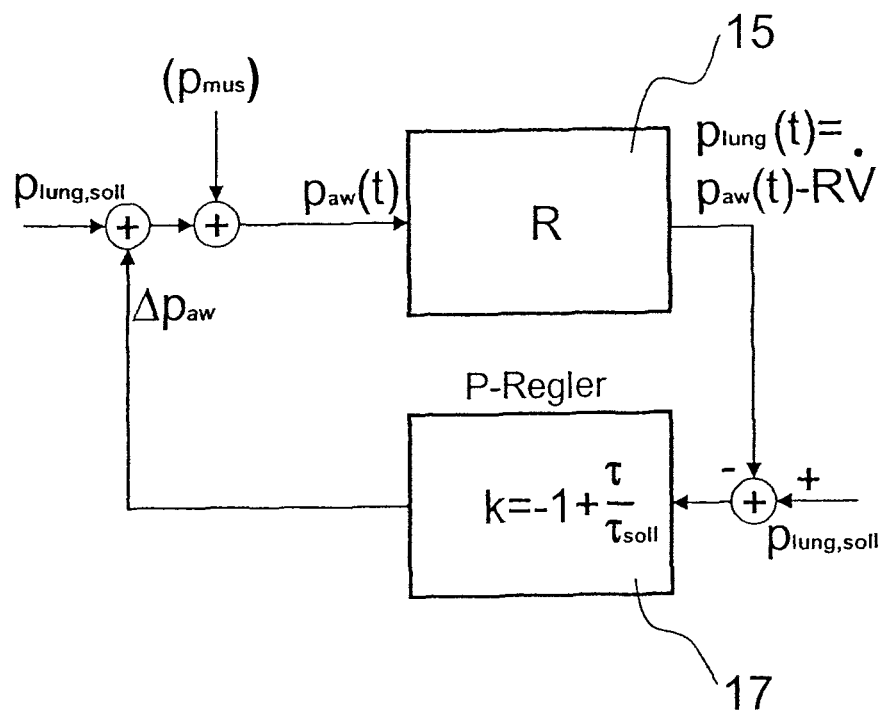
FIG. 3 is a schematically simplified view showing exemplary regulation for the use of the device according to the present invention and of the process according to the present invention.

FIG. 3 shows a possible regulation for the use of the device according to the present invention and for carrying out the process according to the present invention using a proportional regulator with a control amplification K and an excess pressure $dp_{aw}$. The value $p_{mus}$ is an interference variable caused by the patient. FIG. 3 is otherwise self-explanatory to the person skilled in the art, especially after the explanations already made above.

To calculate the pulmonary internal pressure $p_{lung(t)}$, a second-power relationship between the flow dV/dt and the airway resistance or the resistance R, but also a linear relationship between the flow and the differential pressure can be optionally selected. In this type of regulation, the stability of the control circuit is guaranteed with certainty by means of a PID (proportional-integral-derivative) controller. Various variants are available for the technical and stable embodiment of the control circuit. Since the target variable of the control circuit of the pulmonary internal pressure $p_{lung(t)}$ is a value calculated from the model hypotheses anyway in this embodiment, regulation on the basis of the model used for the control system is a preferred process. The parameters of this model may change continuously or on and off because of the differences in the positioning of the patient or because of an episodic change in the pulmonary pathways (for example, because of an asthma attack) and are therefore continuously checked and possibly corrected for correct regulation. To make it possible to guarantee stable regulation by means of a PID controller in every case (taking leakages and possibly additional volumes as well as individual patient parameters into account), it is advantageous to keep the control amplification low. Should greater leakages develop, these can be taken into account in the model in a manner known to the person skilled in the art. This approach offers an additional advantage due to the fact that the resistance R can be used without the noise or the invasiveness of a shutter in case of a higher control amplification selected because of the jump-back in the respiration pressure, which can be used as a step function.

A FUZZY (fuzzy logic) control can respond to nonlinear or time-variant variables especially flexibly and effectively and is therefore also proposed in a preferred embodiment according to the present invention.

In case of leakage, the leak flow should be determined as exactly as possible or rather underestimated, because the calculated pulmonary internal pressure $p_{lung(t)}$ is now calculated as being too high. The actual pulmonary internal pressure $p_{lung(t)}$ is rather too low than dangerously high in this manner, because the desired pulmonary target pressure $p_{lung,soll}$ is allegedly more likely to be reached.

An especially high stability of the control circuit can be achieved by a model-based control, in which the behavior of the model is simulated on the model and the results of the simulation are extrapolated to the inspiratory pressure $p_{aw(t)}$ applied. The model is subsequently improved on the basis of the actual results.

A special advantage of the present invention is that it is possible to perform reliable respiration while reaching the desired end-inspiratory pressure plateau in a short time in case of non-invasive respiration, when volume limitations cannot be used because of high leak flows (for example, in case of the use of fabric masks).

When a model-based control is used, there always are possibilities of checking the model hypotheses for correctness. Thus, the leak rate can be determined by the flow at the end of the phase of expiration. By measuring the flow at the end of the phase of expiration, the intrinsic PEEP or a possibly occurring "air trapping" can be determined. The model hypotheses are, furthermore, not correct if the inspiration value $p_{aw(t)}$ does not correspond to the pulmonary internal pressure $p_{lung(t)}$ after taking all interference variables into account during the plateau phase.

A plurality of processes may also be used according to the present invention to determine the resistance R simultaneously and the results of these determinations can be compared to check the model hypotheses.

Thus, the present invention proposes, for the first time ever, a device for supplying a patient with breathing gas, in which an initially high initial pressure $p_{aw(0)}$ applied from the outside is automatically lowered by means of a control circuit to a lower inspiratory pressure $p_{aw(t)}$ in order to prevent a pulmonary internal pressure $p_{lung(t)}$ from exceeding a predetermined pulmonary target pressure $p_{lung\,sol}$. Overinflation of the lungs due to the respiration is thus ruled out according to the present invention. The device according to the present invention permits, moreover, rapid filling of the lungs with breathing gas and thus makes possible a comparatively long phase of expiration. The present invention proposes, furthermore, a process for regulating a respirator. It shows, moreover, a process for respirating a patient.

While specific embodiments of the invention have been shown and described in detail to illustrate the application of the principles of the invention, it will be understood that the invention may be embodied otherwise without departing from such principles.

What is claimed is:

1. A device for supplying a patient with breathing gas for setting a desired pulmonary target pressure ($P_{lung,soll}$), the device comprising:
   a breathing gas delivery means for delivering breathing gas with an inspiratory pressure ($P_{aw(t)}$);
   internal pressure determination means for determining a pulmonary internal pressure ($P_{lung(t)}$) during a respiration cycle;
   means for setting one of the pulmonary target pressure ($P_{lung,soll}$) that is desired during the phase of inspiration and the inspiratory pressure ($P_{aw(t)}$) to an initial pressure ($P_{aw(t=0)}$) above said pulmonary target pressure ($P_{lung,soll}$), said pulmonary target pressure corresponding to a predetermined lung pressure; and
   control device for regulating said inspiratory pressure ($P_{aw(t)}$) on the basis of said pulmonary internal pressure ($P_{lung(t)}$) and said pulmonary target pressure ($P_{lung,soll}$), said pulmonary internal pressure corresponding to a pressure at an interior surface of one or more lungs of the patient.

2. A device in accordance with claim 1, wherein said control device lowers said inspiratory pressure ($P_{aw(t)}$) from said initial pressure ($P_{aw(t=0)}$) as a function of the difference between said pulmonary target pressure ($P_{lung,soll}$) and said pulmonary internal pressure ($P_{lung(t)}$) determined.

3. A device in accordance with claim 1, wherein said means for setting sets a maximum inspiratory pressure ($P_{aw,max}$).

4. A device in accordance with claim 1, wherein said internal pressure determination means includes measuring means for measuring a change in flow (d(dV/dt)) and a resistance (R).

5. A device in accordance with claim 4, wherein said pulmonary internal pressure ($P_{lung(t)}$) is determined from said change in flow (d(dV/dt)) as well as said resistance (R).

6. A device in accordance with claim 4, wherein said resistance is determined by means of a change in pressure and the change in flow (d(dV/dt)), which can be measured at a time of a transition from said initial pressure ($P_{aw(t=0)}$) to one of a lower value, said pulmonary target pressure ($P_{lung,soll}$) and a lower pressure.

7. A device in accordance with claim 4, wherein said resistance (R) is discarded if said flow (dV/dt) does not equal zero when said pulmonary internal pressure ($P_{lung(t)}$) and said pulmonary target pressure ($P_{lung,soll}$) are equal, wherein an estimated value for said resistance (R) is determined based on said discarded resistance.

8. A device in accordance with claim 1, wherein a flow (dV/dt) equaling zero is reached by means of one or more shutters to determine said pulmonary internal pressure ($P_{lung(t)}$).

9. A device in accordance with claim 8, wherein said resistance (R) determined is discarded if said inspiratory pressure ($P_{aw(t)}$) that becomes established after a plateau phase ($t_1$-$t_2$) has been reached does not equal said pulmonary target pressure ($P_{lung,soll}$) when said flow (dV/dt) is not equal to zero, and wherein the result is used to obtain an estimated value for said resistance (R).

10. A device in accordance with claim 1, wherein said control device has a continuous or discrete controller with P (proportional), I (integral) and/or D (derivative) components.

11. A device in accordance with claim 1, wherein said control device has a FUZZY control.

12. A device in accordance with claim 1, wherein said control device has a model-based control.

13. A device in accordance with claim 1, wherein said control device has a calculation-based leakage compensation.

14. A process for regulating a device for supplying a patient with breathing gas by setting a desired pulmonary target pressure ($P_{lung,soll}$), the process comprising the steps of:
   setting a predetermined initial pressure ($P_{aw(t=0)}$) of a device-side inspiratory pressure ($P_{aw(t)}$) to a value above the pulmonary target pressure ($P_{lung,soll}$), said pulmonary target pressure corresponding to a predetermined internal lung pressure;
   determining at least a pulmonary internal pressure ($P_{lung(t)}$) at least once during a respiration cycle, said pulmonary internal pressure ($P_{lung(t)}$) corresponding to a pressure operative at an interior surface of at least one lung of the patient; and
   lowering said inspiratory pressure ($P_{aw(t)}$) from said initial pressure ($P_{aw(t=0)}$) as a function of the difference between said pulmonary target pressure ($P_{lung,soll}$) and said pulmonary internal pressure ($P_{lung(t)}$) determined.

15. A process in accordance with claim 14, wherein said inspiratory pressure ($P_{aw(t)}$) is lowered to or below said pulmonary target pressure ($P_{lung,soll}$).

16. A process in accordance with claim 14, wherein a maximum inspiratory pressure ($P_{aw,max}$) is set on said device.

17. A process in accordance with claim 14, wherein said pulmonary internal pressure ($P_{lung(t)}$) is determined from a change in flow (d(dV/dt)) as well as a resistance R.

18. A process in accordance with claim 17, wherein said resistance (R) is determined by means of the value of a change in said inspiratory pressure ($P_{aw}$) and a change in flow (d(dV/dt)), which are measured during the transition from said initial pressure ($P_{aw(t=0)}$) to one of a lower value, said pulmonary target pressure ($P_{lung,soll}$) and a lower pressure.

19. A process in accordance with claim 17, wherein said resistance (R) determined is discarded if said flow (dV/dt) does not equal zero when said pulmonary internal pressure ($P_{lung(t)}$) and said pulmonary target pressure ($P_{lung,soll}$) are equal, wherein an estimate of said resistance is determined based on said discarded resistance.

20. A process in accordance with claim 17, wherein a flow (dV/dt) equaling zero is reached by means of one or more shutters to determine said pulmonary internal pressure ($P_{lung(t)}$).

21. A process in accordance with claim 17, wherein said resistance (R) determined is discarded if said inspiratory pressure ($P_{aw(t)}$) that becomes established after a plateau phase ($t_1$-$t_2$)) has been reached does not equal said pulmonary target pressure ($P_{lung,soll}$) at a flow (dV/dt), and this result is used to obtain a better estimate of said resistance (R).

22. A process in accordance with claim 14, wherein said inspiratory pressure ($P_{aw(t)}$) is lowered as a function of, in proportion to the difference between said pulmonary internal pressure ($P_{lung(t)}$) and said pulmonary target pressure ($P_{lung,soll}$), the change in this difference over time and/or the difference integrated over time.

23. A process in accordance with claim 22, wherein the difference between said pulmonary internal pressure ($P_{lung(t)}$) and said pulmonary target pressure ($P_{lung,soll}$), the change in this difference over time and/or the difference integrated over time are discretized.

24. A process in accordance with claim 23, wherein said inspiratory pressure ($P_{aw(t)}$) is lowered when the difference between said pulmonary internal pressure ($P_{lung(t)}$) and said pulmonary target pressure ($P_{lung,soll}$) drops below a predetermined threshold value.

25. A process in accordance with claim 14, wherein the lowering of said inspiratory pressure ($P_{aw(t)}$) is carried out with the use of a FUZZY control.

26. A process in accordance with claim 14, wherein the lowering of said inspiratory pressure ($P_{aw(t)}$) is carried out with the use of a model-based control.

27. A process in accordance with claim 14, wherein calculation-based leakage compensation is taken into account during the regulation of said inspiratory pressure ($P_{aw(t)}$).

28. A process for the respiration of a patient, the process comprising the steps of:
   connecting a breathing gas delivery means to a patient for delivering breathing gas with an inspiratory pressure ($P_{aw(t)}$);
   delivering the breathing gas to the patient with said breathing gas delivery means, wherein an internal pulmonary pressure ($P_{lung(t)}$) is provided at an interior surface of one or more lungs of the patient;
   determining said pulmonary internal pressure ($P_{lung(t)}$) at least once during a respiration cycle;
   providing a means for setting one of a pulmonary target pressure ($P_{lung,soll}$) that is desired during the phase of inspiration and the inspiratory pressure ($P_{aw(t)}$) to an initial pressure ($P_{aw(t=0)}$) above said pulmonary target pressure ($P_{lung,soll}$), said pulmonary target pressure corresponding to a predetermined internal lung pressure; and
   regulating said inspiratory pressure ($P_{aw(t)}$) on the basis of said pulmonary internal pressure ($P_{lung(t)}$) and said pulmonary target pressure ($P_{lung,soll}$).

* * * * *